(12) United States Patent
Zufelt (10) Patent No.: US 8,858,603 B1
(45) Date of Patent: Oct. 14, 2014

(54) CERVICAL PLATE WITH SCREW RETENTION CLIP (75) Inventor: Nephi A. Zufelt, Knoxville, TN (US)

(73) Assignee: Choice Spine, L.P., Knoxville, TN (US)

( * ) Notice: Subject to any disclaimer, the term of this patent is extended or adjusted under 35 U.S.C. 154(b) by 523 days.

(21) Appl. No.: 12/796,984

(22) Filed: Jun. 9, 2010

(51) Int. Cl.
A61B 17/80 (2006.01)

(52) U.S. Cl.
USPC .......................................... 606/289

(58) Field of Classification Search
USPC ......... 606/104, 279, 280, 281, 286–291, 295, 606/296, 305
See application file for complete search history.

(56) References Cited

U.S. PATENT DOCUMENTS

| | | | |
|---|---|---|---|
| 2,847,889 A * | 8/1958 | Cain ............................ 81/424.5 |
| 4,957,497 A | 9/1990 | Hoogland et al. |
| 5,364,399 A | 11/1994 | Lowery et al. |
| 5,607,426 A | 3/1997 | Ralph et al. |
| 5,676,666 A | 10/1997 | Oxland et al. |
| 5,681,311 A | 10/1997 | Foley et al. |
| 5,951,558 A | 9/1999 | Fiz |
| 5,954,722 A | 9/1999 | Bono |
| 5,964,762 A | 10/1999 | Biedermann et al. |
| 6,117,173 A | 9/2000 | Taddia et al. |
| 6,193,721 B1 | 2/2001 | Michelson |
| 6,224,602 B1 | 5/2001 | Hayes |
| 6,235,033 B1 | 5/2001 | Brace et al. |
| 6,241,731 B1 | 6/2001 | Fiz |
| 6,258,089 B1 | 7/2001 | Campbell et al. |
| 6,261,291 B1 | 7/2001 | Talaber et al. |
| 6,306,136 B1 | 10/2001 | Baccelli |
| 6,306,139 B1 | 10/2001 | Fuentes |
| 6,331,179 B1 | 12/2001 | Freid et al. |
| 6,342,055 B1 | 1/2002 | Eisermann et al. |
| 6,402,756 B1 | 6/2002 | Ralph et al. |
| 6,413,259 B1 | 7/2002 | Lyons et al. |
| 6,428,542 B1 | 8/2002 | Michelson |
| 6,454,771 B1 | 9/2002 | Michelson |
| 6,503,250 B2 | 1/2003 | Paul |
| 6,533,786 B1 | 3/2003 | Needham et al. |
| 6,599,290 B2 | 7/2003 | Bailey et al. |
| 6,602,255 B1 * | 8/2003 | Campbell et al. ............. 606/290 |
| 6,652,525 B1 | 11/2003 | Assaker et al. |
| 6,669,700 B1 | 12/2003 | Farris et al. |
| 6,679,883 B2 | 1/2004 | Hawkes et al. |
| 6,695,846 B2 | 2/2004 | Richelsoph et al. |
| 6,755,833 B1 | 6/2004 | Paul et al. |
| 6,945,973 B2 | 9/2005 | Bray |
| 7,001,389 B1 | 2/2006 | Navarro et al. |
| 7,004,944 B2 | 2/2006 | Gause |
| 7,077,843 B2 | 7/2006 | Thramann et al. |
| 7,118,573 B2 | 10/2006 | Michelson |
| 7,204,837 B2 | 4/2007 | Paul |
| 7,273,481 B2 | 9/2007 | Lombardo et al. |
| 7,288,094 B2 | 10/2007 | Lindemann et al. |
| 7,306,605 B2 | 12/2007 | Ross |

(Continued)

FOREIGN PATENT DOCUMENTS

WO 0078238 A1 12/2000
WO 2006/138500 A2 12/2006

Primary Examiner — Christian Sevilla
(74) Attorney, Agent, or Firm — Luedeka Neely Group, PC (57) ABSTRACT An implant system includes a pair of fasteners, a plate, and a horseshoe-shaped clip member. The clip member is located within a recess of the plate and is shaped so as to cooperate with the recess so that lobes of the clip block installed fasteners from backing out, yet, the lobes may be purposefully be deflected to enable removal of fasteners if desired.

7 Claims, 10 Drawing Sheets

(56) References Cited

U.S. PATENT DOCUMENTS

| | | |
|---|---|---|
| 7,309,340 B2 | 12/2007 | Fallin et al. |
| 7,318,825 B2 | 1/2008 | Butler et al. |
| 7,322,984 B2 | 1/2008 | Doubler et al. |
| 7,452,370 B2 | 11/2008 | Anderson |
| 2004/0210217 A1* | 10/2004 | Baynham et al. ............ 606/61 |
| 2006/0217725 A1* | 9/2006 | Suh ............................. 606/71 |
| 2008/0097443 A1 | 4/2008 | Campbell |
| 2011/0152944 A1 | 6/2011 | Campbell et al. |

\* cited by examiner

CERVICAL PLATE WITH SCREW RETENTION CLIP

FIELD

The present disclosure relates to implants for osteosynthesis. More particularly, the disclosure relates to implants for osteosynthesis, particularly spinal osteosynthesis, having improved screw insertion and retention structure.

BACKGROUND

Osteosynthesis relates to surgical procedures that stabilize bone structures and joins the ends of fractured bones utilizing mechanical devices including metal plates, pins, rods, wires or screws. In the field of spinal osteosynthesis, various attempts have been made to provide vertebral stabilizing plates. One problem with conventional spinal osteosynthesis plates relates to enabling desired positioning of the plate relative to the spine using screws to secure the plate adjacent the vertebrae. Another problem relates to preventing installed screws from backing out while also enabling installed screws to be purposefully removed. While various attempts have been made to provide suitable implants for spinal osteosynthesis, improvement is desired.

In accordance with the present disclosure, there is provided an osteosynthesis implant system having improved screw insertion and retention structure.

SUMMARY

The above and other needs are met by an osteosynthesis implant system. In one embodiment, the implant system includes a pair of fasteners, a plate, and a horseshoe-shaped clip member.

The plate has two fastener apertures arranged as a lateral pair and into which the fasteners are installed, and an interior recess within the plate between the lateral pair of the apertures. The recess includes a flat edged receiver and the plate including a slot defined along a portion of each aperture adjacent the recess.

The horseshoe-shaped clip member has a central base from which extends opposed curved lobes, the base having a rear substantially flat edged projection received by and engaging the flat edged receiver of the interior recess of the plate. The flat edged receiver of the plate cooperates with the projection of the base of the clip to substantially retain the clip in a fixed position within the plate, with portions of the lobes of the clip member extending out of the recess via the slots so as to extend into each aperture of the lateral pair of apertures a sufficient distance so as to substantially prevent the head of the fastener within one of the apertures from backing out of or otherwise passing out of the aperture once the screw has been installed.

The system advantageously enables desired positioning of a plate relative to the spine using fasteners to secure the plate adjacent the vertebrae. The system is also advantageously configured to provide a physical barrier to prevent fasteners from backing out, while also enabling fasteners to be readily removed if desired.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

With reference to the drawings, the disclosure relates to an osteosynthesis implant system 10 having a plate 12, a fastener, such as a screw 14, and a screw retention clip 16.

The structure of the system 10 enables desired positioning of the plate 12 relative to the spine using fasteners, such as the screws 14, to secure the plate 12 adjacent the vertebrae. The system is also advantageously configured to provide a physical barrier to prevent the screws 14 from backing out, while also enabling one or more of the screws 14 to be removed if desired.

The plate 12 is desirably configured as an anterior cervical plate for being implanted for use in spinal osteosynthesis. However, it will be understood that the plate 12 may be otherwise configured for engaging other bones for osteosynthesis. The plate 12 is constructed of bio-compatible rigid material, such as titanium, and has a curvature along its longitudinal plane to generally conform to the natural lordosis of the spinal area to which it is applied. The plate 12 is also curved across the transverse plane to conform in shape to the vertebrae to which it is applied. The plate 12 may have additional geometric aspects so as to closely conform to the site to which it is applied, and may also have some bendability to permit some degree of customization.

The plate 12 includes one or more central pin holes 20 located on the plate 12 and of a key-hole shape for receiving temporary fixation pins. The plate 12 also includes a plurality of bone screw apertures 22, each of the bone screw apertures 22 extending through the plate 12 and being configured for receiving one of the screws 14. The bone screw apertures 22 are located at the corners and edges of the plate 12, and arranged in lateral pairs. It will be understood that the plate 12 may be made to different sizes, such as from having only two of the apertures 22 up to having ten or twelve of the apertures 22. Each of the apertures 22 is substantially cylindrical, and includes a smaller diameter rim 24 at the lower end thereof that is smaller than the head of the screw 14 to provide a stop to prevent passage of the head of the screw 14. The shape of the apertures 22 in conjunction with the shape of the screw head as described below allows the screws 14 to be installed into the spinal column at various and different angles as may be required during an osteosynthesis procedure. This is advantageous to enable desired positioning of the plate 12 relative to the spine using the screws 14 to secure the plate 12 adjacent the vertebrae.

An interior recess 26 is defined within the plate 12 between each lateral pair of the apertures 22. The recess 26 is configured for cooperating with the screw retention clip 16, as explained below. A slot 28 is defined along a portion of each aperture 22 adjacent the recess 26 to permit the clip 16 to extend into the apertures 22, as also explained below. To reduce weight and avoid unnecessary bone contact, one or more void areas 30 may be provide through the plate 12.

Figure 7:
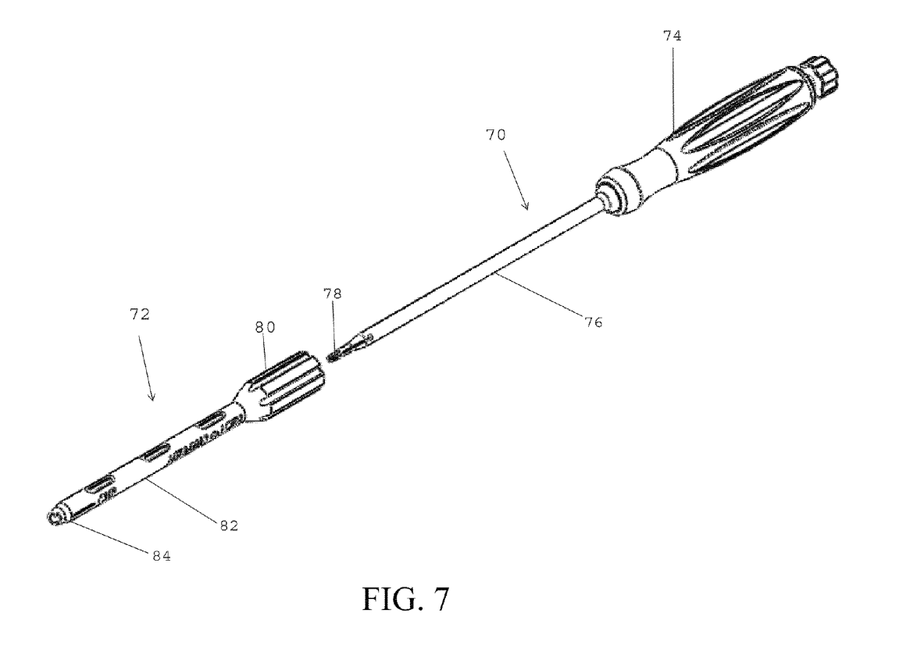
FIG. 7 is an exploded perspective view of a tool device for installation and removal of screws of the system of FIG. 1.
Figure 8:
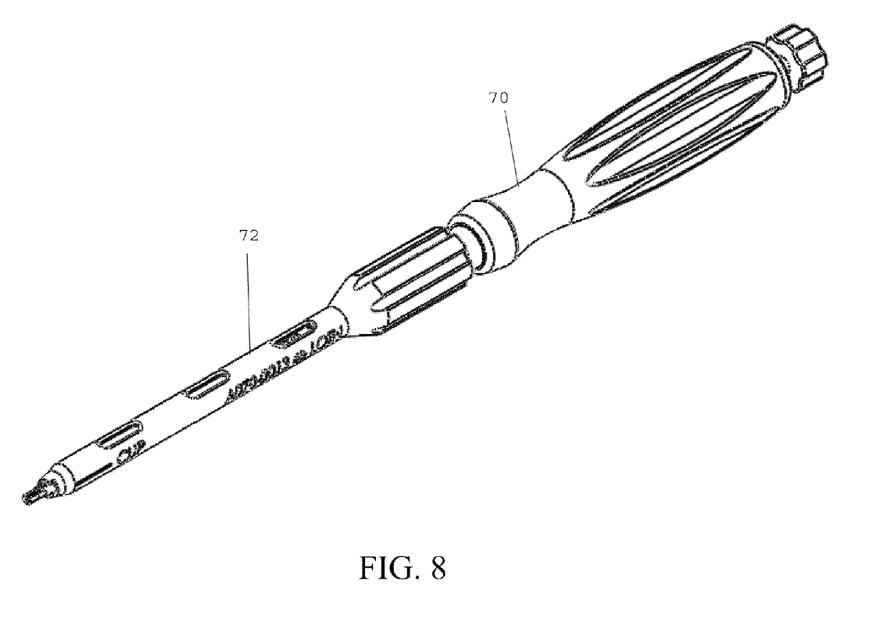
FIG. 8 is an assembled view.
Figure 9:
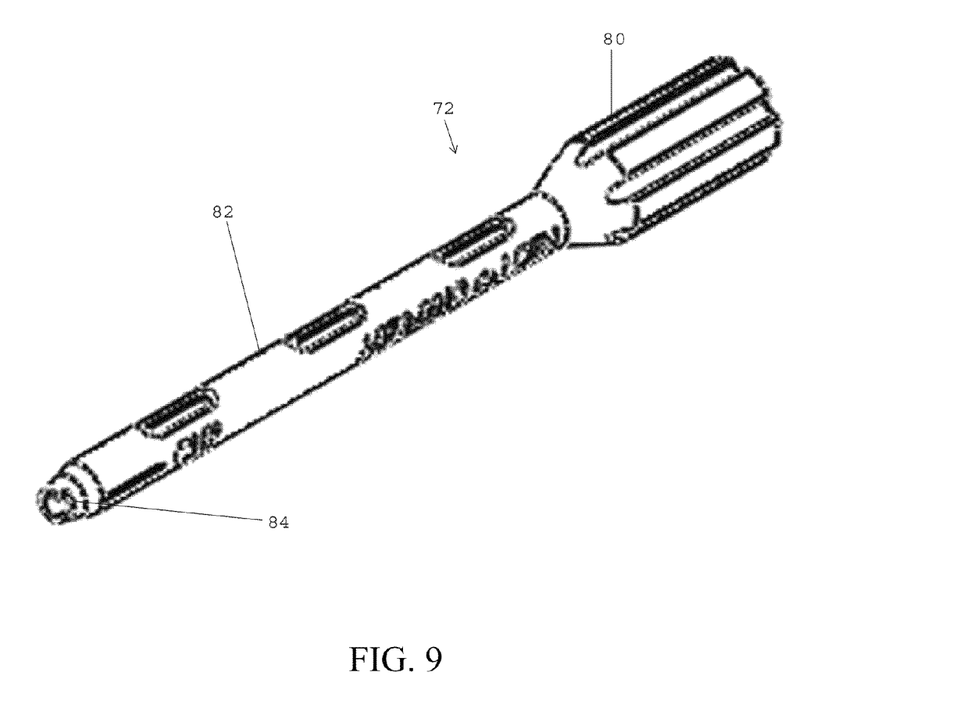
FIG. 9 is a close up view of a removal sleeve of the tool device of FIG. 7.
Figure 10:
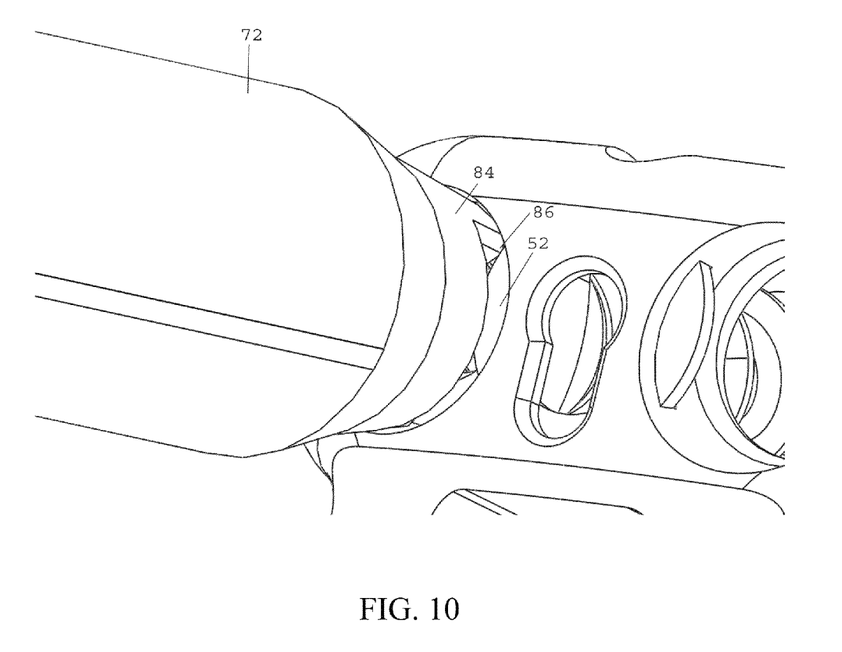
FIG. 10 shows interaction of the removal sleeve with one of the screw retention components.

The screw 14 is a bone screw preferably made of the same material as the plate 12. The screw 14 has an enlarged and head 40 having a central portion 42 configured for receiving a driver or other tool, such as a hexagonal driver 70, discussed below (FIG. 7). The head 40 of the screw 14 also includes a tapered exterior sidewall 44 that contacts the rim 24 and cooperates with the rim 24 to permit installation of the screw 14 at various angles as may be required during an osteosynthesis procedure. Below the head 40, the screw 14 includes a threaded shaft 46 having a self-tapping tip 48 to facilitate penetration of the screw 14 into the bone.

Figure 1:
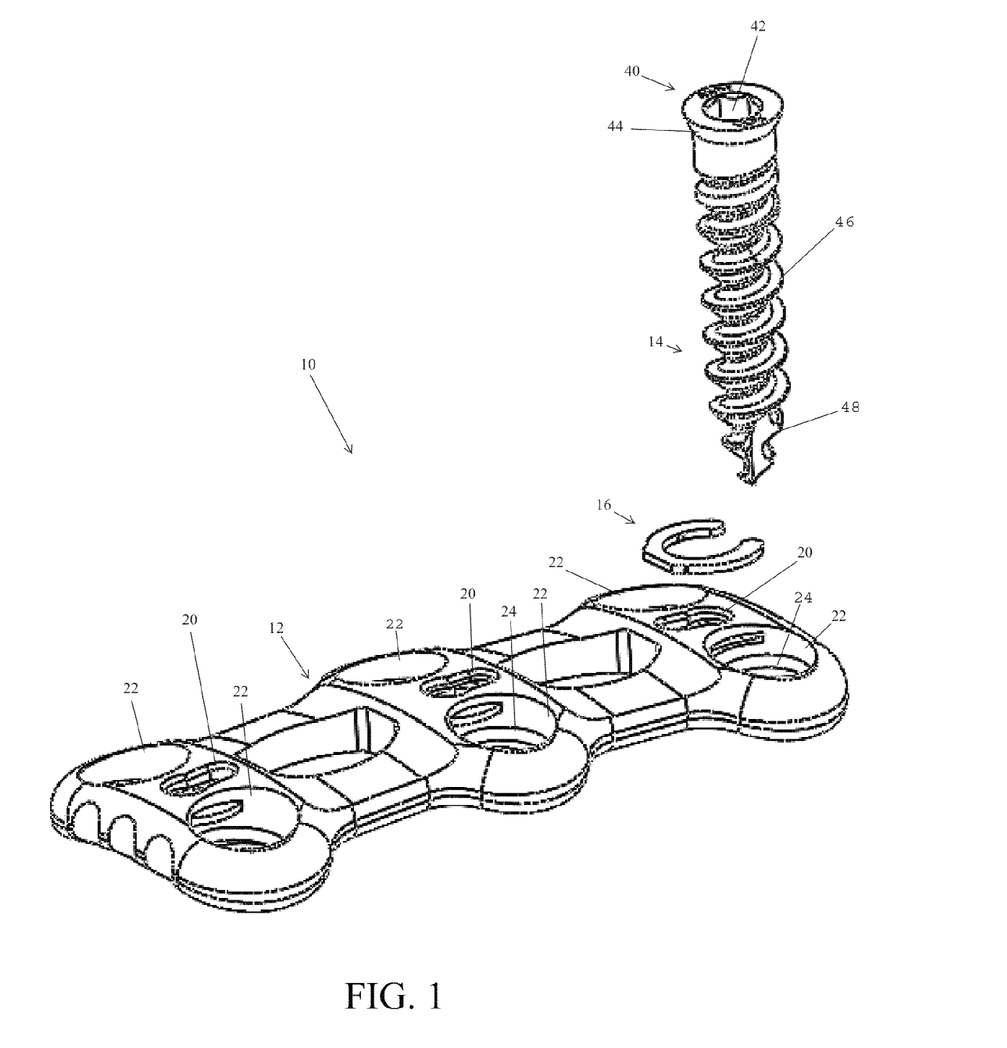
FIG. 1 is an exploded perspective view of an osteosynthesis implant system according to the disclosure.
Figure 2:
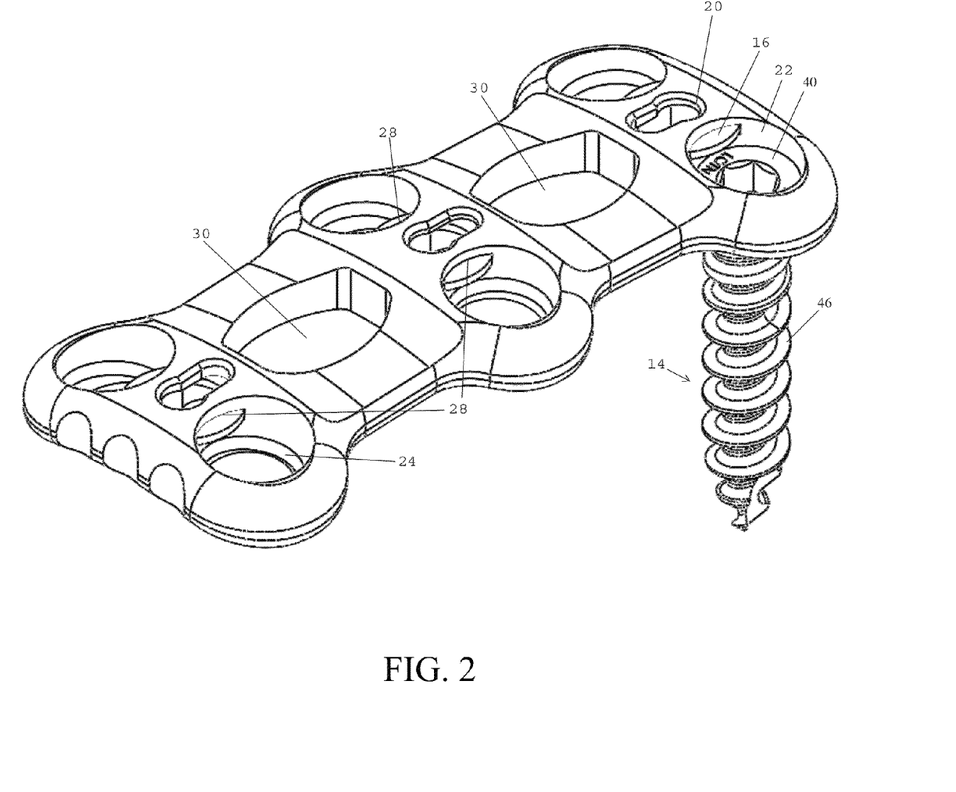
FIG. 2 shows the system of FIG. 1 with the exploded components installed.
Figure 3:
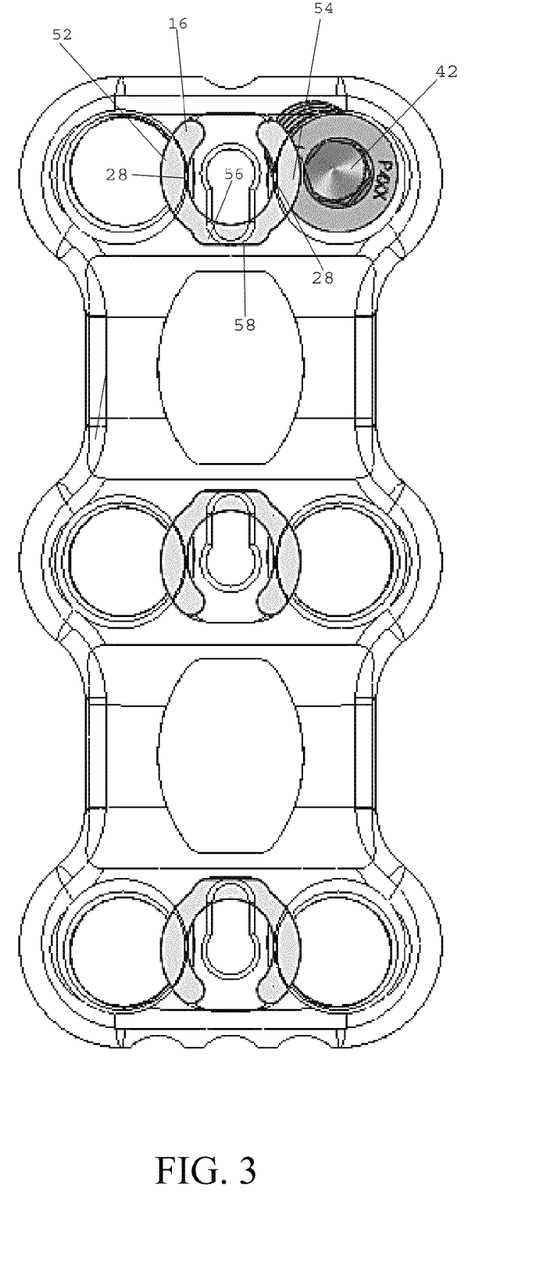
FIG. 3 is a top plan view of the system of FIG. 2.
Figure 4:
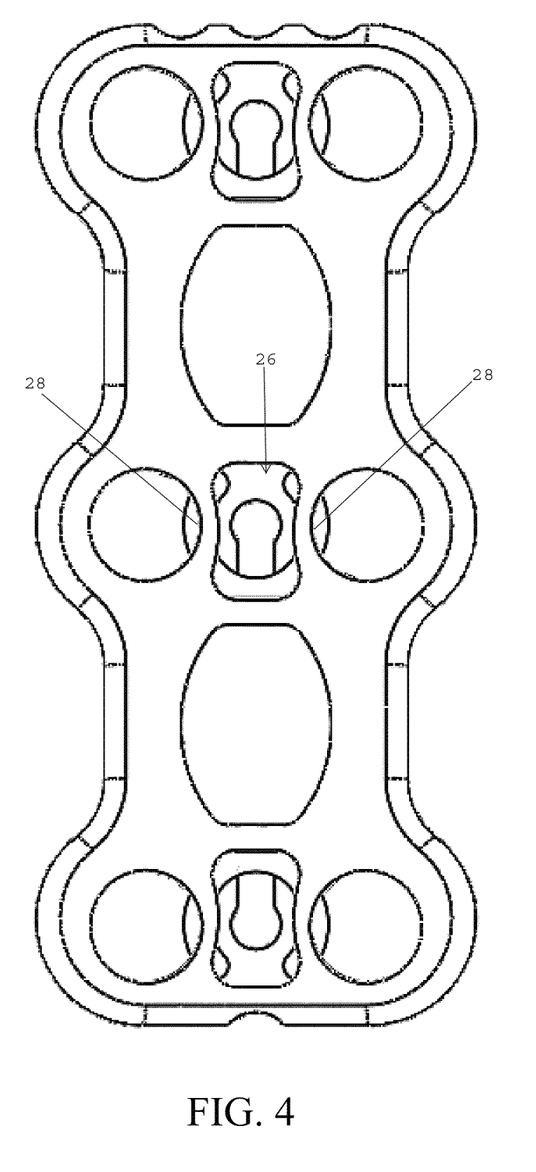
FIG. 4 is a bottom plan view of the system of FIG. 2.
Figure 5:
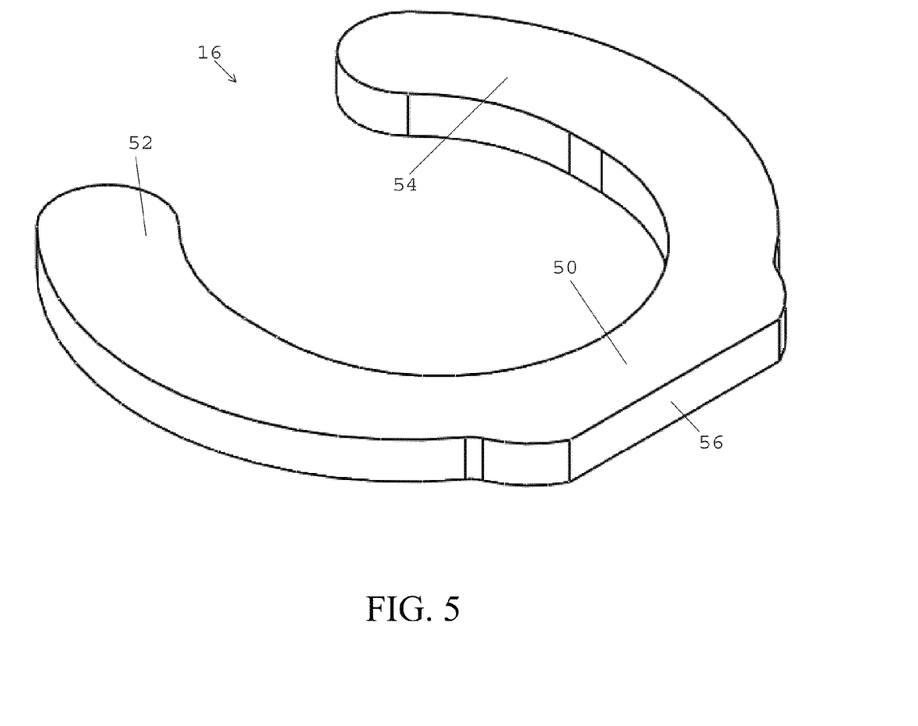
FIG. 5 is a perspective view of a screw retention clip component of the system of FIG. 1.
Figure 6:
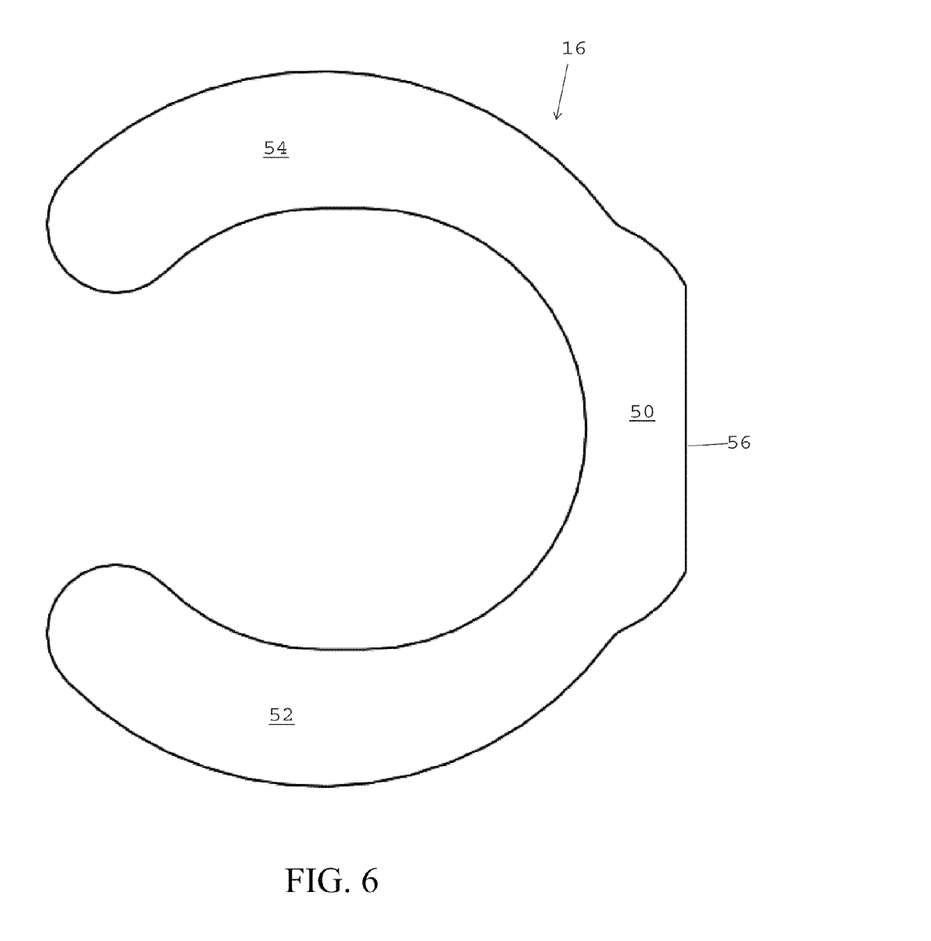
FIG. 6 is a top plan view of the clip of FIG. 5.

The screw retention clip 16 is of once-piece construction and made of an elastic bio-compatible material such as nickel titanium, also known as nitinol, which is a metal alloy of nickel, titanium, and other trace elements with nickel and titanium comprising more than 99% of the total material mass. The clip 16 is in the form of a horseshoe-shaped member, having a central base 50 from which extend opposed curved lobes 52 and 54. The base 50 has a rear substantially flat edged projection 56 configured to be received by and engage a corresponding flat edged receiver 58 of the interior recess 26 of the plate 12 (FIG. 3). The receiver 58 cooperates with the projection 56 of the base 50 to substantially retain the clip 16 in a fixed position, with portions of the lobes 52 and 54 extending out of the recess 26 via the slots 28 so as to extend into the apertures 22 a sufficient distance so as to substantially prevent the head 40 from backing out of or otherwise passing out of the aperture 22 once the screw 14 has been installed. The structure of the clip 16 and the plate 12 with the cooperating projection 56 and receiver 58 enables each of the lobes 52 and 54 functions independently of the other to retain a screw. As explained below, a tool device is provided to enable a lobe 52 or 54 of the clip 16 to be deflected from its normal orientation of extending into the apertures 22 so as to enable removal of a screw if desired.

With reference to FIGS. 7-10, there is shown a tool device for installation and removal of screws of the implant system 10. The tool device includes a driver 70 and a removal sleeve 72 that is slidably inserted over the driver 70 for cooperating with the screw retention clip 16 for removal of installed screws. The driver 70 includes a handle 74, an elongate shaft 76 extending from the handle 74, and a driver structure, such as a hexagonal bit 78, located at the distal end of the shaft 76 and configured to engage the central portion 42 of the head 40 of the screw 14. The removal sleeve 72 includes a connector 80 that snap-fits onto, but is rotatably positionable relative to the lower end of the handle 74 of the driver 70. The removal sleeve 72 also includes a shaft sleeve 82 that receives the shaft 76 of the driver 70, and a keyed end 84 at the distal end of the sleeve 82 that cooperates with the screw retention clip 16 covering an installed screw 14 so as to enable the bit 78 of the driver 70 to be used to remove the screw.

During an osteosynthesis procedure, the plate 12 of appropriate size for the particular spinal anatomy is placed on the vertebral bodies to be treated and temporarily fixed in position as by the insertion of temporary fixation pins into one or more of the central pin holes 20 located on the plate 12. Next, the screws 14 are installed. It will be understood that other procedures may be used for preparing the bone and inserting the screws, however, for the purpose of example, the bone may be initially prepared as positioning an awl or other boring tool in one of the apertures 22 and operating the awl to penetrate the cortex of the vertebral body to create a pilot hole for the screw 14. The screw 14 is then placed in the pilot hole and threadably advanced using the driver 70 until the screw 14 is fully seated in the plate 12 and secured by the clip 16. The tapered sidewall 44 cooperates with the clip 16 to enable the screw head 40 to pass by the clip 16. When the screw 14 is fully seated, the clip 16 covers a portion of the top of the screw head 40. Each of the screws 14 to be installed are installed in this manner such that the clip 16 covers a portion of the top of the screw head 40 of each screw 14 to inhibit backing out of the screw 14.

If it is desired to remove or reposition the screw 14, the removal sleeve 72 is installed on the driver 70 and the keyed end 84 of the sleeve 72 is placed so that a notched edge 86 thereof (FIG. 10) contacts an edge of the clip 16. The sleeve 72 is then rotated or twisted clockwise to deflect the clip 16 away from covering the head 40 of the screw 14, while the driver 70 is turned counter-clockwise to remove the screw 14.

Accordingly, it will be appreciated that the structure of the system 10 enables desired positioning of a plate relative to the spine using screws to secure the plate adjacent the vertebrae. The structure is also advantageously configured to provide a physical barrier to prevent screws from backing out, while also enabling screws to be removed if desired.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. An implant system, comprising:
a pair of fasteners for being installed into a bone, each fastener having a head;
a plate having two fastener apertures arranged as a lateral pair and into which the fasteners are installed, the plate including an interior recess within the plate between the lateral pair of the apertures, the recess including a flat edged receiver and the plate including a slot defined along a portion of each aperture adjacent the recess; and
a horseshoe-shaped clip member having a central base from which extends opposed curved lobes, the base having a rear substantially flat edged projection received by and engaging the flat edged receiver of the interior recess of the plate, the horseshoe-shaped clip member having an open end located between the opposed curved lobes at an opposite end of the horseshoe-shaped clip member from the central base, wherein the flat edged receiver of the plate cooperates with the flat edged projection of the base of the horseshoe-shaped clip member to substantially retain the horseshoe-shaped clip member in a fixed position within the plate, with portions of the lobes of the horseshoe-shaped clip member extending out of the recess via the slots so as to extend into each aperture of the lateral pair of apertures a sufficient distance so as to substantially prevent the head of the fastener within one of the apertures from backing out of or otherwise passing out of the aperture once the fastener has been installed.

2. The system of claim 1, wherein the plate comprises a cervical plate for being implanted for use in spinal osteosynthesis.

3. The system of claim 1, wherein each aperture is substantially cylindrical and includes a smaller diameter rim at a lower end thereof that is smaller than the head of the fastener to provide a stop to prevent passage of the head of the fastener, and wherein the head of the fastener includes a tapered exterior sidewall that contacts the rim when the fastener is installed and cooperates with the rim to permit installation of the fastener at various angles.

4. The system of claim 1, wherein one or both of the lobes of the horseshoe-shaped clip member may be deflected from its normal orientation of extending into the apertures so as to enable removal of one or more of the fasteners if desired.

5. The system of claim 4, further comprising a tool for facilitating removal of one or more of the fasteners, the tool including a notched edge positionable to contact an edge of the horseshoe-shaped clip member, wherein the tool may be twisted to deflect the horseshoe-shaped clip member away from covering the head of the fastener.

6. The system of claim 1, wherein the fasteners comprise bone screws.

7. The system of claim 1, wherein the horseshoe-shaped clip member is made of nitinol.

\* \* \* \* \*